United States Patent [19]

Bender et al.

[11] Patent Number: 4,709,026
[45] Date of Patent: Nov. 24, 1987

[54] KETOSULTAMS

[75] Inventors: Albert Bender, Nuremberg; Dieter Guenther, Kelkheim, both of Fed. Rep. of Germany

[73] Assignee: Hoechst Aktiengesellschaft, Fed. Rep. of Germany

[21] Appl. No.: 831,291

[22] Filed: Feb. 20, 1986

[30] Foreign Application Priority Data

Feb. 23, 1985 [DE] Fed. Rep. of Germany ....... 3506435

[51] Int. Cl.$^4$ .............................................. C07D 279/02
[52] U.S. Cl. ....................................................... 544/3
[58] Field of Search ............................................. 544/3

[56] References Cited

U.S. PATENT DOCUMENTS 4,095,983  6/1978  Wolff et al. ............................... 96/77
4,448,988  5/1984  Guenther ................................ 564/95

OTHER PUBLICATIONS

"Handbook of Chemistry and Physics"—The Chemical Rubber Co., (1973–1974), 54th Edition, pp. C-352 and C-582.
Bender et al., "Liebigs Annalen der Chemie", (1985), vol. 1985—No. 3—Mar., pp. 579–588.

Primary Examiner—John M. Ford
Attorney, Agent, or Firm—Schwartz, Jeffery, Schwaab, Mack, Blumenthal & Evans

[57] ABSTRACT

Method and composition for a ketosultam of the general formula

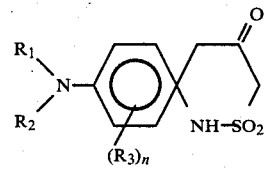

in which $R_1$ and $R_2$ are identical or different and each denote hydrogen, ($C_1$ to $C_8$)-alkyl, which is optionally substituted by one or several halogen atoms, hydroxy groups, cyano groups or ($C_1$ to $C_4$)-alkoxy groups, or phenyl, $R_3$ denotes hydrogen or a ($C_1$ to $C_4$)-alkyl group or ($C_1$ to $C_4$)-alkoxy group, n is a number from 1 to 4, or $R_1$, $R_2$ and $R_3$, together with the corresponding aminophenyl group, denote julolidinyl or N-($C_1$ to $C_3$)-alkylcarbazol-3-yl. The compounds are used in the preparation of sensitizers and dyes.

2 Claims, No Drawings

KETOSULTAMS

DISCLOSURE OF THE INVENTION

The present invention relates to novel ketosultams and to a process for their preparation.

The ketosultams according to the invention have the general formula I

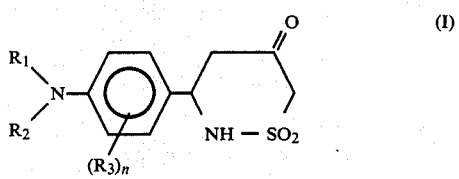

in which $R_1$ and $R_2$ are identical or different and each denote hydrogen, ($C_1$ to $C_8$)-alkyl, which is optionally substituted by one or several halogen atoms, hydroxy groups, cyano groups or ($C_1$ to $C_4$)-alkoxy groups, or phenyl, $R_3$ denotes hydrogen or a ($C_1$ to $C_4$)-alkyl group or ($C_1$ to $C_4$)-alkoxy group, n is a number from 1 to 4, or $R_1$, $R_2$ and $R_3$ together with the corresponding aminophenyl group, denote julolidinyl or N-($C_1$ to $C_3$)-alkylcarbazol-3-yl.

Preference is given to compounds, in which $R_1$ denotes methyl, ethyl or ω-chloroethyl, $R_2$ denotes methyl or ethyl, $R_3$ denotes hydrogen or methoxyl, n is 1, or $R_1$, $R_2$ and $R_3$ together with the corresponding aminophenyl group, denote julolidinyl.

The present invention also relates to a process for the preparation of the ketosultams corresponding to the general formula I, which is characterized in that 4-amino-benzaldehydes of the formula II, in which $R_1$, $R_2$, and $R_3$ and n have the above-indicated meanings, are reacted, in an acid solvent, with 2-oxopropane sulfonamide of the formula III, and the reaction product is then isolated and purified by recrystallization. For formulae II and III, see attached Table of Formulae. A preferred acid solvent is a lower aliphatic alcohol saturated with hydrogen chloride. A further suitable acid-containing solvent is aqueous hydrochloric acid having a concentration of at least 20% by weight.

Isolation can be performed by neutralizing the acid solution by means of a base, whereby the solution can optionally first be concentrated by distilling off the solvent.

Suitble bases include inorganic bases, such as alkali metal carbonates or alkaline earth carbonates, alkali metal hydrogen carbonates or alkaline earth hydrogen carbonates, or alkali metal hydroxides or alkaline earth hydroxides.

Following the neutralization step, the compounds of the formula I according to the invention are usually present as precipitates. They can thus be isolated by filtration and purified by recrystallization.

DETAILED DESCRIPTION OF THE PREFERRED EMODIMENTS

The ketosultams according to the present invention are prepared by reacting appropriately substituted 4-amino-benzaldehydes of formula II and an 2-oxopropane sulfonamide represented by formula III, such as has been disclosed by German Offenlegungsschrift No. 31 16 129, in ethanol saturated with hydrogen chloride, at a temperature between about 0° C. and about 80° C., preferably between about 20° C. and about 40° C.

The ketosultams according to this invention can be used as intermediate products in the preparation of sulfone-containing styrene derivatives which are useful as sensitizers or dyes.

These styrene derivatives are the subject of copending U.S. patent application Ser. No. 831,450 filed on even date and which is incorporated by reference.

The invention is explained in greater detail by way of the following examples.

EXAMPLES 1–4

0.1 mol of 2-oxopropane sulfonamide (III) and 0.1 mol of the corresponding 4-amino-benzaldehyde (II) were stirred for 4 hours in 100 ml of ethanol saturated with hydrogen chloride, at a temperature of 30° C. Then the solvent was distilled off, and the residue was dissolved in water and neutralized with a solution of sodium bicarbonate. The product was filtered off and recrystallized from isopropanol, whereby colorless crystals were obtained. The products were characterized as shown in the tables below:

TABLE 1

| Example No. | $R_1$ | $R_2$ | $R_3$ | Fp (°C.) | Yield % |
|---|---|---|---|---|---|
| 1 | ω-Chloroethyl | methyl | H | 168–170 | 47 |
| 2 | ethyl | ethyl | H | 168 | 71 |
| 3 | julolidinyl | | | 173–177 | 32 |
| 4 | methyl | methyl | 2-methoxyl | 205–208 | 54 |

The results of the elementary analyses of the above compounds are compiled below:

TABLE 2

| Example | Molecular formula (molar weight) | Calc.: Found: | C | H | N | S | Cl |
|---|---|---|---|---|---|---|---|
| 1 | $C_{14}H_{19}N_2SO_3Cl$ (331,66) | | 49.5 49.4 | 5.7 5.7 | 8.4 8.3 | 9.7 10.0 | 10.7 10.6 |
| 2 | $C_{14}H_{20}N_2SO_3$ (296,21) | | 56.8 56.9 | 6.8 6.9 | 9.5 9.7 | 10.8 10.7 | — |
| 3 | $C_{16}H_{20}N_2SO_3$ (300,32) | | 57.3 57.6 | 6.7 6.7 | 9.3 9.1 | 10.7 10.6 | — |
| 4 | $C_{13}H_{18}N_2SO_3$ (282,20) | | 55.3 55.2 | 6.4 6.5 | 9.9 9.9 | 11.4 11.2 | — |

The following Example 5 demonstrates that the compounds of the invention can also be prepared in an aqueous solution of hydrogen chloride:

EXAMPLE 5

0.1 mol of 2-oxopropane sulfonamide (III) and 0.1 mol of 4-diethyl-amino-benzaldehyde (II) were stirred for 5 hours in 80 ml of 35% strength hydrochloric acid at a temperature of 30° C. The mixture was then neutralized to a pH of 7 with sodium hydroxide solution. The precipitate was filtered off, washed with water and recrystallized from isopropanol. 14 g (yield: 48%) of the compound No. 2 of Table 1 were obtained.

TABLE OF FORMULAE

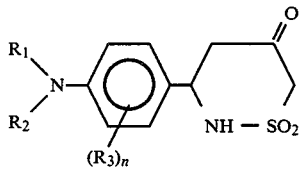   I

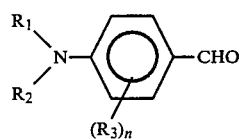   II

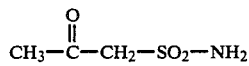   III

What is claimed is:

1. A ketosultam having the formula:

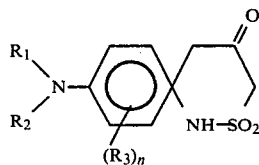   I wherein
$R_1$ and $R_2$ are the same or different, and each is selected from the group consisting of a hydrogen atom, a phenyl group and a $C_1$-to-$C_8$ alkyl group which can be unsubstituted or substituted by at least one from the group consisting of a halogen atom, a hydroxyl group, a cyano group and an alkoxy group having 1 to 4 carbon atoms,
$R_3$ is a hydrogen atom, a $C_1$-to-$C_4$ alkyl group or a $C_1$-to-$C_4$ alkoxy group,
n is a number from 1 to 4 or
$R_1$, $R_2$ and $R_3$, together with the aminophenyl radical of said ketosultam to which each is substituted, all form a julolidinyl radical or a N-($C_1$-to-$C_3$)-alkyl-carbazol-3-yl radical.

2. A ketosultam as claimed in claim 1, wherein
$R_1$ is methyl, ethyl or ω-chloroethyl,
$R_2$ is methyl or ethyl,
$R_3$ is hydrogen or methyoxy,
n is 1, or
$R_1$, $R_2$, and $R_3$, together with the amino-phenyl radical of said ketosultam to which each is substituted, all form a julolidinyl radical.

* * * * *